US006987111B2

(12) United States Patent
Greco et al.

(10) Patent No.: US 6,987,111 B2
(45) Date of Patent: Jan. 17, 2006

(54) ARIPIPRAZOLE, OLANZAPINE AND HALOPERIDOL PAMOATE SALTS

(75) Inventors: Kristyn Greco, N. Quincy, MA (US); James Wright, Lexington, MA (US)

(73) Assignee: Alkermes Controlled Therapeutics, II, Cambridge, MA (US)

( * ) Notice: Subject to any disclaimer, the term of this patent is extended or adjusted under 35 U.S.C. 154(b) by 278 days.

(21) Appl. No.: 10/635,232

(22) Filed: Aug. 6, 2003

(65) Prior Publication Data

US 2005/0032836 A1 Feb. 10, 2005

(51) Int. Cl.
*A61K 31/445* (2006.01)
*A61K 31/495* (2006.01)

(52) U.S. Cl. .................. 514/253; 514/327; 424/422; 424/426; 544/363; 546/217

(58) Field of Classification Search ........... 514/253, 514/327; 424/422, 426; 544/363; 546/217
See application file for complete search history.

(56) References Cited

U.S. PATENT DOCUMENTS

| | | | |
|---|---|---|---|
| 4,076,942 | A | 2/1978 | Smith et al. |
| 5,445,832 | A | 8/1995 | Orsolini et al. |
| 5,656,299 | A | 8/1997 | Kino et al. |
| 5,723,467 | A | 3/1998 | Mesens et al. |
| 5,776,885 | A | 7/1998 | Orsolini et al. |
| 6,245,346 | B1 | 6/2001 | Rothen-Weinhold et al. |
| 2003/0027816 | A1 | 2/2003 | Allen et al. |

FOREIGN PATENT DOCUMENTS

| | | |
|---|---|---|
| WO | WO 02/069941 A1 | 9/2002 |
| WO | WO 2004/017970 * | 3/2004 |

OTHER PUBLICATIONS

Saias et al. "Pamoates, a class of oral drugs with delayed and prolonged effect" Ann. Pharm. Franc. 27(9-10)557-70 (1970).*
Diamond "Human metabolization of amitriptyline tagged with carbon-14" CA 63:5869 (1965).*
Coleman et al. "The disposition of pyrimethanmine . . . " CA 105:143 (1986).*
Gido et al. "Conventional versus novel conditions . . . " CA 120:38005 (1994).*
Randell et al. "Prolonged analgesia after epidural . . . " CA 122:46222 (1995).*

* cited by examiner

*Primary Examiner*—Celia Chang
(74) *Attorney, Agent, or Firm*—Elmore, Craig & Vanstone, PC; Carolyn Elmore

(57) ABSTRACT

The invention relates to the discovery that pamoate salts of haloperidol and aripiprazole result in a good to superior long acting and/or extended release profile. Thus, in one aspect of the invention, the invention includes pamoate salts of haloperidol or aripiprazole. Preferably, the pamoate salt is characterized by a ratio of haloperidol to pamoate of 1:1 or 2:1. The pamoate salt can be crystalline, such as a needle or a dense crystal, such as described in the Figures.

The invention further relates to methods of treating an individual in need thereof comprising administering a pharmaceutical composition comprising a pamoate salt of haloperidol and aripiprazole.

15 Claims, 4 Drawing Sheets

ARIPIPRAZOLE, OLANZAPINE AND HALOPERIDOL PAMOATE SALTS

BACKGROUND OF THE INVENTION

Polymeric sustained release devices of various antipsychotic agents have been described. However, such sustained release devices tend to be costly to manufacture and difficult to produce. Thus, there still exists a need for improved methods of delivering such agents which maximize the pharmacological profile of the active agent and can be produced in a more cost effective manner.

SUMMARY OF THE INVENTION

The invention relates to the discovery that pamoate salts of haloperidol, olanzapine and aripiprazole result in a good to superior long acting and/or extended release profile. Thus, in one aspect of the invention, the invention includes pamoate salts of haloperidol, olanzapine or aripiprazole. Preferably, the pamoate salt is characterized by a ratio of drug, e.g., haloperidol, to pamoate of 1:1 or 2:1. The pamoate salt can be crystalline, such as a needle or a dense crystal, such as described in the Figures.

The invention further relates to methods of treating an individual in need thereof comprising administering a pharmaceutical composition comprising a pamoate salt of haloperidol and aripiprazole.

DETAILED DESCRIPTION OF THE INVENTION

The invention relates to the discovery that pamoate salts of haloperidol, olanzapine and aripiprazole result in a good to superior long acting and/or extended release profile. Thus, in one aspect of the invention, the invention includes pamoate salts of haloperidol, olanzapine or aripiprazole. Preferably, the pamoate salt is characterized by a ratio of drug, e.g., haloperidol, to pamoate of 1:1 or 2:1. The pamoate salt can be crystalline, such as a needle or a dense crystal, such as described in the Figures.

The invention further relates to methods of treating an individual in need thereof comprising administering a pharmaceutical composition comprising a pamoate salt of haloperidol, olanzapine and aripiprazole.

Alternatively, similar active agents, such as the carbostyril compounds described in U.S. Pat. Nos. 5,006,528 or 4,734,416, which are incorporated herein by reference can be used to manufacture the pamoate salts of the invention.

The ionization equilibria of organic bases are illustrated below:

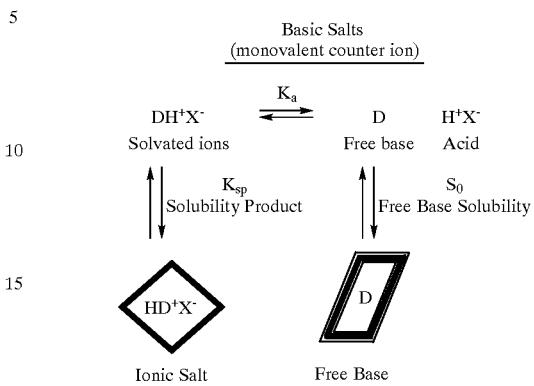

The chemical process shown is composed of the acid dissociation constant ($K_a$), the free base solubility and the salt solubility product ($K_{sp}$). Under alkaline conditions the free base form is the stable form. As the pH of the solution is lowered the fraction of drug ionized and the aqueous solubility increases. At high concentrations of ionized drug (protonated amine) the solubility product of the salt ($K_{sp}$) will be exceeded and the salt form will precipitate out. The nature of the drug and counterion determine the $K_{sp}$ and the associated solid state properties of the salt.

The chemical structure and ionization equilibrium for haloperidol, a basic drug, is

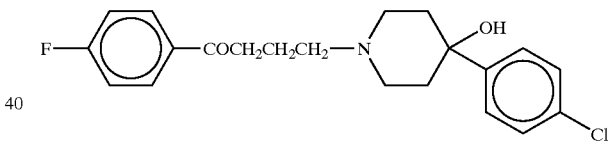

MW=376, MP=148° C., $pK_a$=8.3

Figure 1:
FIG. 1 depicts two salt forms of haloperidol pamoate.
Figure 2:
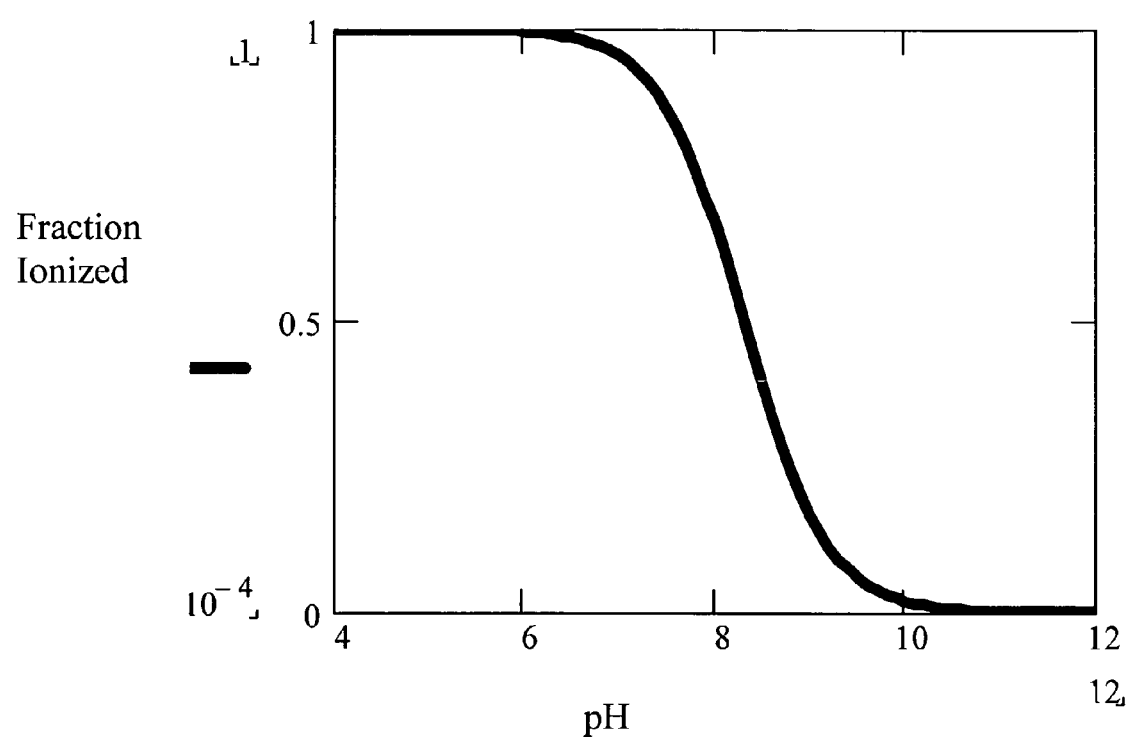
FIG. 2 shows the ionization profile of the drug as a function of pH. At pH values above 9 the drug is predominantly in the unionized state, while at pH values below the $pK_a$ the drug becomes positively charged.

FIG. 2 shows the ionization profile of the drug as a function of pH. At pH values above 9 the drug is predominantly in the unionized state, while at pH values below the $pK_a$ the drug becomes positively charged. The protonated form of the drug coupled with an appropriate counterion allows for the formation of an ionic salt.

There are a wide range of counterions that have been used to prepare salts of bases. The most frequently used anion to form a salt of a basic drug is the hydrochloride form. Two examples of carboxylic acid counterions used in pharmaceutical salts are:

Structure of Tartaric acid MW=150, $pK_{a1}$=3.02, $pK_{a2}$=4.36

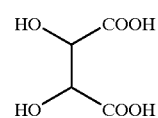

Structure of Pamoic acid: MW=388, $pK_{a1}$=2.51, $pK_{a2}$=3.1

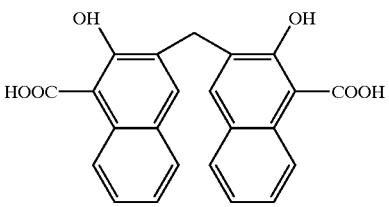

Figure 3:
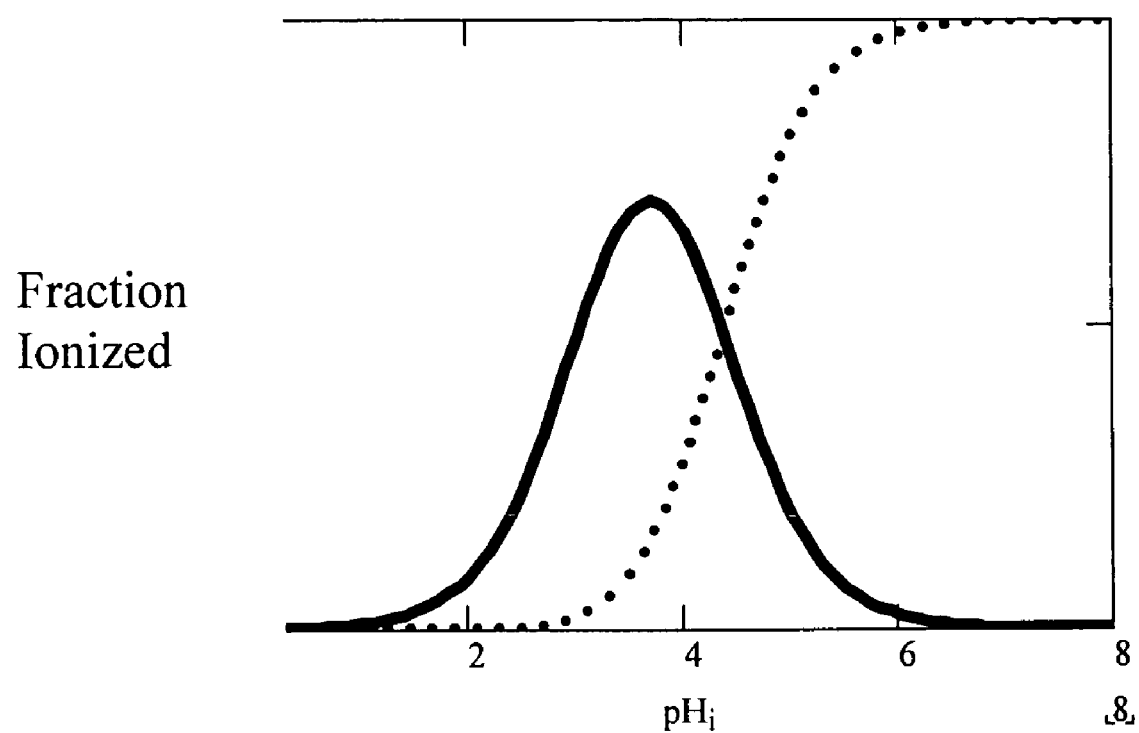
FIGS. 3 and 4 show the ionic equilibrium of tartrate and pamoate; the monoanion is depicted with the solid line and the dianion is depicted with the dotted line.
Figure 4:
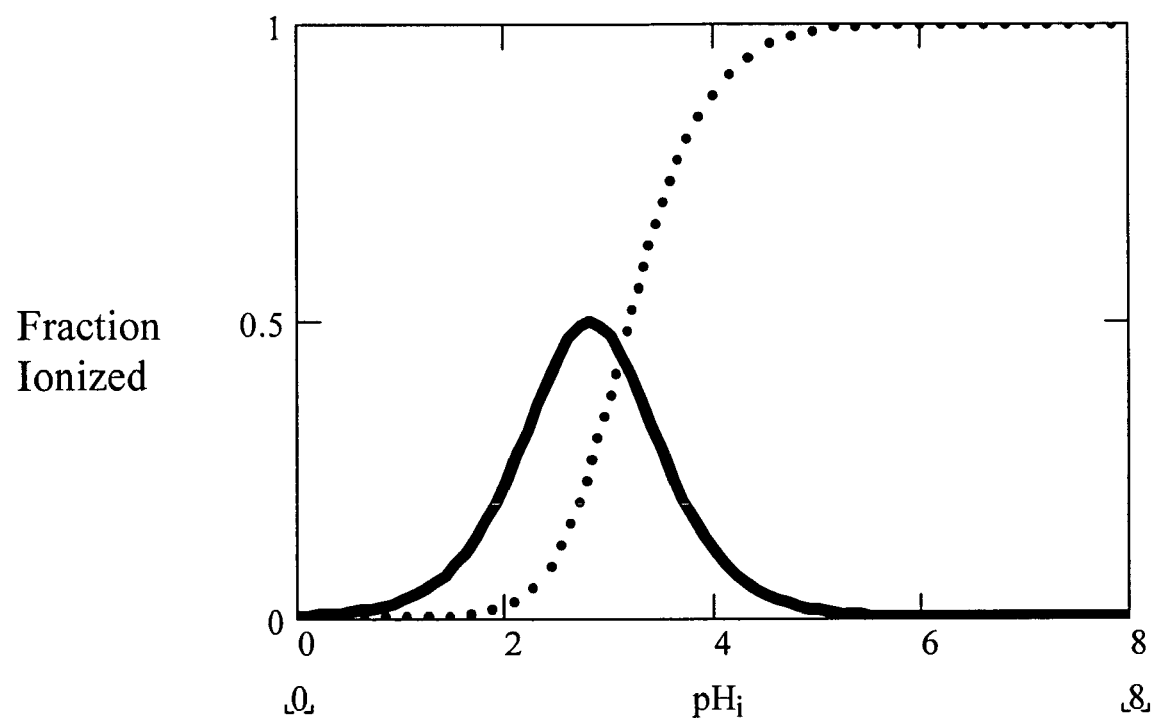

The ionic equilibrium is shown in FIGS. 3 and 4. Two counterions give a wide range in solubility properties for tartrate and pamoate. It is noted that each of these counterions is divalent. Thus salts that are 1:1 and 2:1 (protonated base:counterion) are possible. The solution conditions that the salt is formed under will dictate which salt form (1:1 or 2:1) will precipitate. The chemical structures illustrate that these two counterions have very different structures and properties. Tartaric acid will provide the salt with high water solubility, while pamoic acid will form salts with limited solubility and thus can be used to retard dissolution. Both water soluble and insoluble forms have use in the development of drug delivery formulations.

The composition of the claimed invention can include various pharmaceutical forms for administration purposes. To prepare the pharmaceutical compositions of this invention, an effective amount of the subject compounds as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration. Administration can include enteral, including oral, or parenteral, including pulmonary, transdermal, subcutaneous or intramuscular injection or implantation. For the latter administration routes, the subject compounds preferably are suspended in an aqueous solvent, which may further comprise a wetting agent, such as the polyoxyethylene derivatives of sorbitan esters, e.g. polysorbate 80 (Tween 80®) and polysorbate 20 (Tween 20®), lecithin, polyoxyethylene- and polyoxypropylene ethers, sodium deoxycholate, and the like; a suspending agent such as a cellulose derivate, e.g. methylcellulose, sodium carboxymethylcellulose and hydroxypropyl methylcellulose, polyvinylpyrrolidone, alginates, chitosan, dextrans, gelatin, polyethylene glycols, polyoxyethylene- and polyoxypropylene ethers and the like; an acid, e.g. hydrochloric acid, and the like; a base, e.g. sodium hydroxide, and the like; a buffer comprising a mixture of appropriate amounts of an acid such as phosphoric, succinic, tartaric, lactic, acetic, maleic or citric acid, and a base, in particular sodium hydroxide or disodium hydrogen phosphate; a preservative, e.g. benzoic acid, benzyl alcohol, butylated hydroxyanisole, butylated hydroxytoluene, chlorbutol, a gallate, a hydroxybenzoate, EDTA, phenol, chlorocresol, metacresol, benzothonium chloride, myristyl-.gamma.-piccolinium chloride, phenylmercuri acetate, thimerosal and the like; a tonicity adjusting agent, e.g. sodium chloride, dextrose, mannitol, sorbitol, lactose, sodium sulfate, and the like. Alternatively, the subject compounds may be formulated in an oil. Appropriate oils for this purpose are fixed oils, for example, peanut oil, sesame oil, cottonseed oil, corn oil, safflower oil, castor oil, ethyloleate, soy bean oil, synthetic glycerol esters of long chain fatty or medium chain acids and mixtures of these and other oils. Also, thickening agents may be added to the composition, e.g. aluminum monostearate, ethylcellulose, triglycerides, hydrogenated castor oil, and the like.

In view of the usefulness of the subject compounds in the treatment of psychotic diseases it is evident that the present invention provides a method of treating warm-blooded animals, in particular humans, suffering from psychotic diseases, said method comprising the administration of a pharmaceutically effective amount of the subject compounds in admixture with a pharmaceutical carrier. In a further aspect, the present invention relates to the use of the subject compounds as a medicine, particularly as an antipsychotic. In general it is contemplated that an effective amount would be from 0.05 mg/kg to 50 mg/kg body weight, more preferably from 0.5 mg/kg to 10 mg/kg body weight.

The active agent is preferably administered in a long acting formulation. In one embodiment the active agent is released from the formulation over a period of at least about 24 hours, preferably about 48 hours.

The active agent can also be administered in an extended release formulation. In one embodiment, the extended release formulation releases the active agent over a period of at least about 7 days, preferably at least about 14 days, alternatively for at least 2, 3, 4, 6 or 8 weeks. The composition is preferably administered by injection, such as intramuscularly or subcutaneously.

In one embodiment, the formulations can be administered as a single or sole dose. However, the invention is particularly beneficial for those individuals that require constant or chronic therapy, such as those that receive repeated doses over several weeks or months or more. In such dosing regimens, the method can comprise a first administration of a first extended release formulation and a second administration of a second extended release formulation. The second formulation can be the same, substantially the same or different as the first and can include the same active agent or a different active agent. For example, the second formulation can be administered at about 7 days, or more, such as at least about 14 days, or at least about 17 days, after the first administration, where the first administration results in the release of agent for a period of 1, 2, 3, 4, 5, 6, 7, 8, 9, 10, 11, 12, 13, 14 days, or more.

The term "therapeutically effective amount" is further meant to define an amount resulting in the improvement of any parameters or clinical symptoms. The actual dose may vary with each patient and does not necessarily indicate a total elimination of all disease symptoms.

As used herein, the term "individual", "subject" or "patient" refers to a warm blooded animal, including but not limited to humans, such as a mammal which is afflicted with a particular disease state.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described for example in Remington's Pharmaceutical Sciences, latest edition, Mack Publishing Co.

Pharmaceutical compositions can be manufactured utilizing techniques known in the art. Typically the therapeutically effective amount of the compound will be admixed with a pharmaceutically acceptable carrier.

The compositions of the present invention may be administered parenterally, such as by injection. Preferred methods of administration include intramuscular and subcutaneous injection, for example.

For parenteral administration the compounds may be dissolved in a physiologically acceptable pharmaceutical carrier and administered as either a solution or a suspension. Viscous injectable carriers are preferred, having for example, a viscosity of at least 20 cp at 20° C. In other embodiments, the fluid phase of the suspension has a viscosity at 20° C. of at least about 30 cp, 40 cp, 50 cp, and 60 cp. The composition may also comprise a viscosity enhancing agent, a density enhancing agent, a tonicity enhancing agent, and/or a wetting agent. Illustrative of suitable pharmaceutical carriers include water, saline, dextrose solutions, fructose solutions, ethanol, or oils of animal, vegetative, or synthetic origin. The pharmaceutical carrier may also contain preservatives, and buffers as are known in the art.

In another embodiment, the formulation can be surgically implanted. Such formulations can include any of the well-known biodegradable and bioerodible carriers, such as poly-lactides and poly-lactide-co-glycolides and collagen formulations. Such materials may be in the form of solid implants, sponges, and the like. In any event, for local use of the materials, the active ingredients usually are present in the carrier or excipient in a weight ratio of from about 1:1000 to 1:20,000, but are not limited to ratios within this range.

Preferably, the compounds are in an extended release formulation. Extended (also referred to as sustained or controlled) release preparations may be achieved through the use of polymers (preferably poly-lactide or poly-lactide-co-glycolide polymers) to entrap or encapsulate the active agent described herein. Extended release formulations can be made by spray drying polymer-drug mixtures, emulsion-based technologies, coacervation based technologies, film casting, extrusion based technologies and other processes to manufacture polymer-drug microparticles possessing an extended release profile. Examples of suitable extended release technologies that can be used to incorporate the agents herein include, without limitation, the MEDISORB® technology, as described in, for example, U.S. Pat. Nos. 6,264,987 to Wright, 5,654,008 and/or 5,792,477, for example; the PROLEASE® technology, as described, for example in U.S. Pat. No. 6,358,443 to Herbert; the technologies described by Southern Research Institute, as described for example in U.S. Pat. No. 6,306,425; and "Method of Preparing Sustained Release Microparticles," U.S. application Ser. No. 60/441,946, filed Jan. 23, 2003, and the technologies described by Alza Corp., including the ALZAMER® Depot injection technology. The contents of these patents are incorporated herein by reference in their entirety.

In one preferred embodiment, the agent is present in the extended release device or formulation in an amount of at least about 5% by weight, preferably at least about 10% by weight, more preferably at least about 30% by weight of the total weight of the device, or formulation.

Also contemplated is the entrapment of the active agent in microparticles prepared, for example, by coacervation techniques or by interfacial polymerization (for example, hydroxymethylcellulose or gelatin-microcapsules and poly-(methylmethacrylate) microcapsules, respectively), in colloidal drug delivery systems (for example, liposomes, albumin, microparticles, microemulsions, nanoparticles, and nanocapsules), or in macroemulsions.

When the composition is to be used as an injectable material, including but not limited to needle-less injection, it can be formulated into a conventional injectable carrier. Suitable carriers include biocompatible and pharmaceutically acceptable solutions.

The following examples are intended to illustrate and not to limit the scope of the present invention.

EXAMPLE 1

The pamoate salt of haloperidol can be prepared by treatment of haloperidol with pamoic acid or pamoate salt in solvent. Haloperidol pamoate can be prepared by adding a solution of haloperidol in an appropriate solvent, eg. ethanol with acetic acid, to a solution of disodium pamoate, pamoic acid or other pamoate salt and leaving undisturbed for 1–3 or more days until precipitation. Alternatively, other methods such as evaporation, slow or fast cooling or stirring solutions can also be used to precipitate salt.

Specifically, 2.5 ml of a 0.1M solution of haloperidol in an acidified ethanol (5% acetic acid) was added to 2.5 ml of a 0.1M solution of disodium pamoate (2.5 ml) in ethanol/water (50/50). The mixture was allowed to sit at room temperature for 1–3 days. The resulting precipitate was filtered off by suction, washed with ethanol and dried in a vacuum oven at 60° C., yielding 240 mg of 1:1 haloperidol pamoate salt.

EXAMPLE 2

2.5 ml of a 0.25M solution of haloperidol in an acidified ethanol (5% acetic acid) was added to 12.5 ml of a 0.05M solution of disodium pamoate in ethanol/water (75/25). The mixture was allowed to sit at room temperature for 1–3 days. The resulting precipitate was filtered off by suction, washed with ethanol and dried in a vacuum oven at 60° C., yielding 206 mg of 2:1 haloperidol pamoate salt.

EXAMPLE 3

2.5 ml of a 0.25M solution of haloperidol in an acidified ethanol (5% acetic acid) was added to 6.25 ml of a 0.1M solution of disodium pamoate in ethanol/water (50/50). The mixture was allowed to sit at room temperature for 1–3 days. The resulting precipitate was filtered off by suction, washed with ethanol and dried in a vacuum oven at 60° C., yielding 264 mg of 2:1 haloperidol pamoate salt.

EXAMPLE 4

5 ml of a 0.05M solution of haloperidol in an acidified ethanol (5% acetic acid) was added to 1 ml of a 0.25M solution of disodium pamoate in ethanol/water (50/50). The mixture was allowed to sit at room temperature for 1–3 days. The resulting precipitate was filtered off by suction, washed with ethanol and dried in a vacuum oven at 60° C., yielding 107 mg of 1:1 haloperidol pamoate salt.

EXAMPLE 5

5 ml of a 0.05M solution of haloperidol in an acidified ethanol (5% acetic acid) was added to 2.5 ml of a 0.1 M solution of disodium pamoate in ethanol/water (50/50). The mixture was allowed to sit at room temperature for 1–3 days. The resulting precipitate was filtered off by suction, washed with ethanol and dried in a vacuum oven at 60° C., yielding 119 mg of 1:1 haloperidol pamoate salt.

EXAMPLE 6

A (0.05–0.5M) solution of aripiprazole in an acidified ethanol is added to a (0.05–0.5M) disodium pamoate solution in a mixture of water/ethanol (100/0–0/100). The mixture is allowed to sit at room temperature for 1–3 days. The resulting precipitate is filtered off by suction, washed with solvent and dried in a vacuum oven at 60° C.

EXAMPLE 7

Pharmacokinetic Evaluation of Haloperidol and Olanzapine in Rats following administration of single subcutaneous doses of Haloperidol and Olanzapine formulations.

Species and Strain: Sprague-Dawley rats. Male; 450+/−50 grams.

Study Groups: 4 Groups. 12 subjects
  Group A: three rats injected once SC with 20 mg of haloperidol bulk drug
  Group B: three rats injected once SC with 40 mg of haloperidol pamoate.
  Group C: three rats injected once SC with 20 mg of olanzapine bulk drug.
  Group D: three rats injected once SC with 50 mg of olanzapine bulk drug.

Route of Injection: Subcutaneous (SC) injection into the interscapular region.

Injection Vehicle: Aqueous Diluent: Water, 3% CMC low viscosity, 0.1% Tween 20, in 0.9% NaCl Dose Volumes: Dose suspensions were formulated as follows:
  Group A: 20 mg powder in 0.75 mL Diluent
  Group B: 40 mg microparticles in 0.75 mL Diluent
  Group C: 20 mg powder in 0.75 mL Diluent
  Group D: 50 mg powder in 0.75 mL Diluent Blood Collection: Blood samples were collected via a lateral tail vein after anesthesia with Halothane. A syringe without an anticoagulant was used for the blood collection, then the whole blood was transferred to tubes containing K2 EDTA and mixing beads (Microtainer®; MFG# BD365974). The blood samples were processed (the tubes are inverted 15–20 times and centrifuged for 2 minutes at >14,000 g's) to separate plasma. The plasma samples prepared in this manner were transferred to labeled plain tubes (Microtainer®; MFG# BD5962) and stored frozen at <−70° C.

Blood Volumes: At least 250 µL blood for each time point during the first 24 hours and 400 µL for each time point thereafter.

Time Points to obtain plasma:

| 2 h | 24 h | 3 d | 10 d* |
|---|---|---|---|
| 4 h | 32 h | 4 d | 14 d* |
| 8 h | 2 d | 7 d | |

*Note:
Only group B had time points taken after day 7. Also, for any group when plasma concentrations are lower than the limit of quantitation, that group was terminated.

The observed results indicate that the pamoate salt exhibited good to excellent extended release profiles.

EXAMPLE 7

Injectable microparticles comprising polymer and pamoate salts can be prepared using an efficient and facile single solvent process. PLG polymer and salt can be co-dissolved in a single solvent; (2) the solvent removed by vacuum drying or sublimation to form a polymer/drug matrix; (3) the matrix milled to produce a powder; (4) the resulting powder compacted to form a compressed matrix; and (5) the compressed matrix milled to form a dense, injectable microparticle formulation. Preferably, the pamoate salt loading can be about 10% or about 30% or more (w/w) of the final weight of the microparticle composition. Solvents, for example, methylene chloride, acetone, dimethylsulfoxide (DMSO), acetonitrile, and ethyl acetate are suitable for use.

Suitable polymers include:

Lactide:Glycolide Ratio; Intrinsic Viscosity; End Group; Solvent

A 30% (w/w) 50:50, 0.75 dL/g; Acid end group; $CH_2Cl_2$

B 30% (w/w) 75:25; 0.60 dL/g; Lauryl ester end group; $CH_2Cl_2$

C 25 30% (w/w) 50:50; 0.61 dL/g; Lauryl ester end group; $CH_2Cl_2$

The pamoate salt/polymer/solvent mixtures can be poured into either a polytetrafluoroethylene flat mold (approximately 1 inch×1 inch×½ inch deep) or a 3 inch diameter jar to form a film, for example. The films can be dried either in an FTS Dura-Dry Lyophilizer (Kinetic Systems, Inc., Santa Clara, Calif.) or in a vacuum oven. Films dried under various conditions including variation of maximum vacuum, ambient pressure, elevated temperature, ambient temperature, and drying time can be made.

The films can be milled using a 24-tooth Retsch Ultra Centrifugal Mill (Retsch, Inc., Newtown, Pa.) operating at 14,000 rpm. The collection pan is filled with liquid nitrogen prior to milling. The resulting powder, collected from the collection pan, is a flowable product that aided subsequent compaction steps. A portion of the powders produced by milling the films can be retained for analysis at this point. These powders can be retained for comparison with the powders made by the subsequent compacting and re-milling of the film powders described below.

A portion of the milled powders can be compacted using a Carver Model C Press (Carver, Inc., Wabash, Ind.) and either about ¼ inch or about ½ inch cylindrical dies. About 50 to about 300 milligrams of milled powder is filled into the dies and compacted at a machine setting of about 5000 pounds for about 30 seconds at room temperature to form pellets.

The compacted matrix is subsequently milled using a 24-tooth Retsch Ultra Centrifugal Mill (Retsch, Inc., Newtown, Pa.) operating at 14,000 rpm. The collection pan is filled with liquid nitrogen prior to milling. The final powder was collected from the collection pan and placed into vials for analysis.

The sustained release compositions described herein can also be prepared by any of emulsion, coacervation, and cryogenic microencapsulation techniques. The general process associated with each technique is described below.

Coacervation-S/O/O Process

The coacervation process, also referred to herein as a solvent-oil-oil (S/O/O) process, requires formation of a solvent-in-oil emulsion with drug and organic polymer solutions. An oil, typically a silicone oil, is then added to the water-in-oil emulsion to induce phase separation and to precipitate the polymer. The embryonic microparticles are then quenched in a solvent that removes the oil and polymer solvent. Pamoate salt is encapsulated in PLG polymer using a solvent-oil-oil (S/O/O) emulsion system. The initial embryonic microparticles was formed in a S/O/O inner emulsion step after which they are subjected to coacervation and hardening steps. The microparticles are collected, dried and filled into vials. Further details of each step in the complete process is set forth below.

Inner Emulsion Formation

A solvent-in-oil emulsion is created using sonication. The solvent phase of the emulsion contained dissolved drug and various excipients. The PLG phase contained polymer dissolved in methylene chloride.

Coacervation Formation

Coacervation can be induced by adding silicone oil at a controlled rate to the inner emulsion with agitation, forming embryonic microparticles. The embryonic microparticles formed are relatively soft and required hardening.

Microparticle Hardening

The embryonic microparticles are added to a heptane/ethanol solvent mixture with gentle agitation. The solvent mixture hardens the embryonic microparticles. After hardening for about one hour at about 3° C., the solvent mixture is decanted and pure heptane was added at 3° C. and mixed for about one hour.

Microparticles Drying and Collection

After the hardening step, the microparticles are transferred and collected on a fine mesh pore-plate inside a drying chamber. A final heptane rinse of the hardening vessel is performed. The microparticles are dried with nitrogen gas over a four-day period with temperature ramping from about 3° C. to about 38° C.

In general, PLG is dissolved in methylene chloride. The inner phase is prepared by dissolving the drug and any excipients in solvent. The solution is then injected into the polymer solution while probe sonicating. The resultant emulsion is then added to an emulsion reactor. Silicone oil (350 centiStokes) is slowly added to the reactor via peristaltic pump with stirring at about 1000 rpm. The mixture is then added to n-heptane. After stirring for about two hours, the microparticles are isolated by filtration and vacuum dried overnight.

Emulsion Process-S/O/W Process

The emulsion process is also referred to as a solvent-oil-water (S/O/W) process. Briefly, a solution of drug is dispersed in a polymer solution which is then emulsified in an outer aqueous phase (e.g., PVA). The microparticles are then hardened in an aqueous quench.

In a typical experiment, PLG (1.96 g) is dissolved in methylene chloride (22.5 g) and drug is dissolved (20 mg drug in 1.75 g solvent). The drug solution is then drawn up in a syringe and injected into the polymer solution while it is probe sonicated. The resultant emulsion is then quickly added to an emulsion reactor containing 125 g aqueous 5% polyvinyl alcohol (PVA). The stir rate of the reactor was set to about 800 RPM. The mixture is stirred for about 1.5 minutes and then added to a water quench (2.8 L at 10° C.). After about two hours in the quench, the hardened microparticles are isolated by filtration and vacuum dried overnight.

Cryogenic Process

The cryogenic process used atomization to form droplets of polymer solution containing drug. Embryonic microparticles are then frozen in liquid nitrogen and the polymer solvent is removed through a subsequent ethanol extraction technique.

The cryogenic processing to produce microparticles includes two steps: (1) the production of a lyophilizate or dried drug substance; and (2) microencapsulation using a low-temperature, non-aqueous technique. Lyophilizates are formulated by atomizing a mixture of drug and excipient using a two-fluid nozzle, freezing the atomized droplets and drying the frozen droplets using lyophilization. It is understood that any suitable methods of drying known in the art can be employed. Specifically, frozen droplets are dried for about 7 days at a primary drying condition of −26° C. shelf and 96 mTorr chamber pressure followed by secondary drying for an additional 3 days at about 20° C. and 0 mTorr.

Pamoate salt containing microparticles can be produced with the cryogenic, non-aqueous process, all at a nominal target load of 10% drug or more. Drug is suspended in an organic solution consisting of 3–20% 4A PLG dissolved in methylene chloride. This suspension is sonicated for about 4 minutes on ice, and then the suspension is atomized using a sonication nozzle and frozen by contacting with liquid nitrogen layered over a bed of frozen ethanol. The sample is warmed to −80° C. in order to allow for microparticle hardening and extraction of solvent. The microparticles are then filtered and dried.

Solid/Oil/Water (S/O/W) and Solid/Oil/Oil (S/O/O) Processes

Solid drug can also be encapsulated using modified versions of the emulsion and coacervation processes described above. These modified processes are referred to solid/oil/water (S/O/W) and solid/oil/oil (S/O/O). For example, solid drug is suspended in methylene chloride containing 3–20% PLG and sonicated for about four minutes on ice. Subsequent processing is conducted in a manner analogous to either the W/O/O or W/O/W methods.

Polymer:

Examples of specific PLG polymers suitable for use are listed below. All of the polymers employed in the following examples are set forth in the list and all listed polymers were purchased from Alkermes, Inc. of Cincinnati, Ohio and can be described as follows:

Polymer 2A: Poly(lactide-co-glycolide); 50:50 lactide:glycolide ratio; 12.3 kD Mol. Wt.; IV=0.15 (dL/g).

Polymer 2A-1: Poly(lactide-co-glycolide); 65:35 lactide:glycolide ratio; 16 kD Mol. Wt.; IV=0.19 (dL/g).

Polymer 2.5A: Poly(lactide-co-glycolide); 50:50 lactide:glycolide ratio; 25kD Mol. Wt.; IV=0.24 (dL/g).

Polymer 3A: Poly(lactide-co-glycolide); 50:50 lactide:glycolide ratio; 47 kD Mol. Wt.; IV=0.38 (dL/g).

Polymer 3.5A: Poly(lactide-co-glycolide); 50:50 lactide: glycolide ratio; Mol. Wt., Not Determined; IV=0.42 (dL/g).

Polymer 4A: Poly(lactide-co-glycolide); 50:50 lactide:glycolide ratio; Mol. Wt. 45–64 kD; IV=0.45–0.47 (dL/g).

Polymer 4A-1: Poly(lactide-co-glycolide); 65:35 lactide: glycolide ratio; Mol. Wt. 53 kD; IV=0.43 (dL/g).

Modifications and variations of the invention will be obvious to those skilled in the art from the foregoing detailed description of the invention. Such modifications and variations are intended to come within the scope of the appended claims.

All patents, patent application publications and articles cited herein are incorporated by reference in their entirety.

We claim:

1. A pamoate salt of haloperidol.
2. The pamoate salt of claim 1 wherein the ratio of haloperidol to pamoate is 1:1 or 2:1.
3. The pamoate salt of claim 1 wherein the salt is a needle.
4. The pamoate salt of claim 1 wherein the salt is crystalline.
5. A pamoate salt of aripiprazole.
6. The pamoate salt of claim 4 wherein the ratio of aripiprazole to pamoate is 1:1 or 2:1.
7. The pamoate salt of claim 5 wherein the salt is crystalline.
8. A method of treating an individual having psychotic diseases comprising administering a pharmaceutical composition comprising a pamoate salt of an active agent selected from the group consisting of haloperidol and aripiprazole.
9. The method of claim 8 wherein the composition is administered by injection.
10. The method of claim 8 wherein the composition is administered intramuscularly or subcutaneously.
11. The method of claim 8 wherein the composition releases an effective amount of the active agent over a period of at least about 24 hours.
12. The method of claim 8 wherein the composition releases an effective amount of the active agent over a period of at least about 48 hours.
13. The method of claim 8 wherein said composition consists essentially of the pamoate salt and a viscous aqueous carrier.
14. The method of claim 8 wherein the extended release formulation comprises a polylactide and the pamoate salt.
15. The method of claim 8 wherein the extended release formulation comprises a polylactide-co-glycolide and the pamoate salt.

* * * * *